(12) United States Patent
Ghosh et al.

(10) Patent No.: US 12,033,753 B2
(45) Date of Patent: Jul. 9, 2024

(54) MEDICAL DEVICE DATA ANALYSIS

(71) Applicant: Micron Technology, Inc., Boise, ID (US)

(72) Inventors: Gitanjali T. Ghosh, Boise, ID (US); Irene K. Thompson, Boise, ID (US); Jessica M. Maderos, Boise, ID (US); Hongmei Wang, Boise, ID (US); Fatma Arzum Simsek-Ege, Boise, ID (US); Kathryn H. Russo, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 401 days.

(21) Appl. No.: 16/989,749

(22) Filed: Aug. 10, 2020

(65) Prior Publication Data

US 2021/0193314 A1   Jun. 24, 2021

Related U.S. Application Data

(60) Provisional application No. 62/951,963, filed on Dec. 20, 2019.

(51) Int. Cl.
*G16H 40/67* (2018.01)
*G16H 10/60* (2018.01)
(Continued)

(52) U.S. Cl.
CPC ............ *G16H 40/67* (2018.01); *G16H 10/60* (2018.01); *G16H 40/63* (2018.01); *G16H 80/00* (2018.01)

(58) Field of Classification Search
CPC ... G06Q 50/20–26; G16H 10/60; G16H 80/00
(Continued)

(56) References Cited

U.S. PATENT DOCUMENTS 5,474,552 A * 12/1995 Palti .................... A61M 5/1723
604/67
8,688,467 B2   4/2014 Harrison
(Continued)

OTHER PUBLICATIONS

Rawassizadeh R, Tomitsch M, Nourizadeh M, Momeni E, Peery A, Ulanova L, Pazzani M. Energy-Efficient Integration of Continuous Context Sensing and Prediction into Smartwatches. Sensors. 2015; 15(9):22616-22645. https://doi.org/10.3390/s150922616 (Year: 2015).*
(Continued)

*Primary Examiner* — Christopher L Gilligan
*Assistant Examiner* — Jessica Marie Webb
(74) *Attorney, Agent, or Firm* — Brooks, Cameron & Huebsch, PLLC (57) ABSTRACT

Systems, apparatuses, and methods related to medical device data analysis are described. In some examples, a medical device is implanted in a user of the medical device and the data generated by the medical device is not easily accessible to the user. In an example, a controller can be configured to receive, by a mobile device coupled to a medical device, data from the medical device, where the data is a part of a baseline dataset related to the medical device. The controller can be configured to receive different data from the medical device, where the different data is received from the medical device as the different data is generated by the medical device, analyze the data from the medical device and the different data generated by the medical device, and perform an action based on the analyzed data and the different data generated by the medical device.

19 Claims, 4 Drawing Sheets

(51) Int. Cl.
  *G16H 40/63* (2018.01)
  *G16H 80/00* (2018.01)
(58) Field of Classification Search
  USPC .......................................................... 705/2, 3
  See application file for complete search history.

(56) References Cited

U.S. PATENT DOCUMENTS

| | | | |
|---|---|---|---|
| 8,727,978 | B2 | 5/2014 | Tran |
| 2003/0139778 | A1 | 7/2003 | Fischell |
| 2005/0017864 | A1 | 1/2005 | Tsoukalis |
| 2011/0105860 | A1* | 5/2011 | Houben ............... A61B 5/0205 607/18 |
| 2017/0072202 | A1* | 3/2017 | Kane ................... A61N 1/36514 |
| 2017/0119317 | A1* | 5/2017 | Thakur ................... G16H 50/20 |
| 2017/0245794 | A1* | 8/2017 | Sharma ................... G16H 20/10 |
| 2018/0060520 | A1* | 3/2018 | Degen .................... G16H 40/63 |
| 2018/0182475 | A1* | 6/2018 | Cossler .................. G16H 50/50 |
| 2018/0200437 | A1* | 7/2018 | Mazlish ............ A61M 5/14248 |
| 2018/0242875 | A1* | 8/2018 | Volpe .................... A61B 5/335 |
| 2018/0350455 | A1* | 12/2018 | Rosen ..................... G16H 80/00 |
| 2019/0008384 | A1* | 1/2019 | Brisben .................. A61B 5/364 |
| 2019/0030350 | A1* | 1/2019 | Finch ....................... G16H 80/00 |
| 2019/0288860 | A1 | 9/2019 | Poltorak |
| 2019/0290172 | A1 | 9/2019 | Hadad et al. |
| 2019/0307335 | A1 | 10/2019 | Bruce |
| 2019/0328256 | A1* | 10/2019 | Badie ..................... G16H 50/30 |
| 2019/0336077 | A1* | 11/2019 | Kuhn ................... A61B 5/7282 |
| 2019/0362841 | A1 | 11/2019 | Aysin et al. |
| 2019/0380610 | A1 | 12/2019 | Bornzin et al. |
| 2019/0384890 | A1 | 12/2019 | Pulitzer et al. |
| 2019/0392924 | A1 | 12/2019 | Bettencourt-Silva et al. |
| 2019/0392931 | A1 | 12/2019 | Abousy et al. |
| 2020/0094061 | A1* | 3/2020 | Ghosh .................... A61B 5/349 |
| 2020/0147401 | A1 | 5/2020 | Hellman et al. |
| 2020/0162948 | A1 | 5/2020 | Pei |
| 2020/0188677 | A1 | 6/2020 | An et al. |
| 2020/0297233 | A1* | 9/2020 | Mitchell .............. A61B 5/7203 |
| 2021/0059568 | A1* | 3/2021 | Gunderson ........... A61B 5/1118 |

OTHER PUBLICATIONS

A. D. Jurik and A. C. Weaver, "Bidirectional ECG Monitoring with an Event Detection Policy Engine," 2012 21st International Conference on Computer Communications and Networks (ICCCN), Munich, Germany, 2012, pp. 1-8, doi: 10.1109/ICCCN.2012.6289216. (Year: 2012).*
International Search Report and Written Opinion from related international application No. PCT/US2020/060881, dated Mar. 11, 2021, 12 pages.

* cited by examiner

MEDICAL DEVICE DATA ANALYSIS

PRIORITY INFORMATION

This application claims priority of U.S. Provisional Application Ser. No. 62/951,963, filed on Dec. 20, 2019, the contents of which are incorporated herein by reference.

TECHNICAL FIELD

The present disclosure relates generally to semiconductor memory and methods, and more particularly, to apparatuses, systems, and methods for medical device data analysis.

BACKGROUND

Medical devices (e.g., implantable medical devices, medical prothesis, etc.) can communicate with scanners, servers, wireless devices, etc. to obtain and exchange information. The medical apparatuses can be implanted into a patient in order to affect biological and/or additional functioning of the patient. Over time, a patient's needs or the effect of the medical apparatus on the patient can change. In order to avoid adverse effects of the medical device on the patient, for example, the medical device can be checked in order to improve operational efficiency, more closely match with a patient's needs or recommendations of a physician by communication with an external device.

Memory devices can be coupled to other devices (e.g., a computing device, a mobile device, etc.) to store (e.g., write) data, commands, and/or instructions for use by the device while the computer or electronic system of the device is operating. For example, data, commands, and/or instructions can be transferred between the device and the memory device(s) during operation of a computing or other electronic system.

Memory devices are typically provided as internal, semiconductor, integrated circuits in computers or other electronic systems. There are many different types of memory including volatile and non-volatile memory. Volatile memory can require power to maintain its data (e.g., host data, error data, etc.) and includes random access memory (RAM), dynamic random access memory (DRAM), static random access memory (SRAM), synchronous dynamic random access memory (SDRAM), and thyristor random access memory (TRAM), among others. Non-volatile memory can provide persistent data by retaining stored data when not powered and can include NAND flash memory, NOR flash memory, and resistance variable memory such as phase change random access memory (PCRAM), resistive random access memory (RRAM), and magnetoresistive random access memory (MRAM), such as spin torque transfer random access memory (STT RAM), among others.

DETAILED DESCRIPTION

Systems, apparatuses, and methods related to medical device data analysis are described. Medical devices can generate data about a user of the medical device and/or the medical device itself. In some examples, the medical device is implanted in a user of the medical device and the data generated by the medical device is not easily accessible to the user. Medical devices can be coupled to computing systems including memory devices to provide information about the medical device to the user of the medical device. One or more memory devices of the computing system can store information about the medical device and/or the user of the medical device such that the information is accessible to the user. In an example, a controller can be configured to receive, by a mobile device coupled to a medical device, data from the medical device, where the data is a part of a baseline dataset related to the medical device. The controller can be configured to receive different data from the medical device, where the different data is received from the medical device as the different data is generated by the medical device, analyze the data from the medical device and the different data generated by the medical device, and perform an action based on the analyzed data and the different data generated by the medical device.

As used herein, storing data can include writing data to a memory media included in a memory device. For example, data can be stored to a memory device by writing the data to a memory media of a memory device. In addition, the data can also be retrieved by a computing device (e.g., a mobile device and/or a controller) from its place of storage. Medical devices can generate data about the health of a user, a body part of a user, and/or the medical device. The data generated by the medical device can be difficult for a user of the medical device to view and/or analyze.

In some previous approaches, data generated by a medical device (e.g., an implantable medical device) can be viewed by a user of the medical device when accompanied by a doctor and/or while located at a medical facility setting. Medical devices may include limited memory storage capabilities, as such, in some instances, data generated by a medical device is not saved by the medical device unless the data is considered problematic. However, a user of a medical device may wish to understand the impact of the medical device on their body when performing non-problematic activities. For example, a user of an implantable medical device such as a pacemaker may want to view data generated by the pacemaker while exercising or performing other routine activities. Further, in some instances a user may experience an ostensibly minor incident (e.g., a minor fall, etc.) and wish to know if the medical device registered an abnormality (e.g., a problem). Not being able to view the data in real-time can lead to frustration, wasted time, anxiety, and/or wasted resources to travel to a medical facility to be informed that the medical device did not store any information about the ostensibly minor incident.

In contrast, as will be described herein, communicatively coupling a medical device to a computing system (e.g., a mobile device) corresponding to a user of the medical device can provide the user with an interface to view data of the medical device. As used herein, "communicatively coupled" can include coupled via various wired and/or wireless connections between devices such that data can be transferred in various directions between the devices. The coupling need not be a direct connection, and in some examples, can be an indirect connection.

In some examples, a computing system can include a mobile device that belongs to the user of the medical device. The mobile device (e.g., a smartwatch) can generate user visible data from a combination of inputs. In some examples, the mobile device can include a display. The display can be a touchscreen display that serves as an input device. When a touchscreen display is touched by a finger, digital pen (e.g., stylus), or other input mechanism, associated data can be received, displayed, and/or transmitted by the mobile device. The touchscreen display may include pictures and/or words, among others that a user can touch to interact with data, the medical device, other computing devices, and/or the mobile device.

The inputs can include data such as settings of the medical device, current user physical data, cloud data, medical device identification data, medical device manufacturing data, biometric data of the user, environmental data, etc. Biometric data can include a height, weight, blood type, heart rate, blood pressure, glucose levels, a level of molecules, chemical compounds, (e.g., drugs, alcohol, etc.) in the blood of the user, histamine production, antibody production, among others. Environmental data can include a geographical location, air pollution information, allergen information, ultraviolet radiation, among others.

In one example embodiment, the mobile device can analyze the data from the medical device by comparing the input data to data generated by the medical device in real time. The analyzed data can be presented on the display of the mobile device. Based on the analysis, the mobile device can take an action. For example, the mobile device can transmit an electronic notification to another computing device corresponding to a user, and/or a medical facility. In some examples a user can interact with the display of the mobile device to transmit the analyzed data to another computing device, to an emergency contact entity (e.g., another person, or emergency services, etc.). In another example, based on the analysis, the mobile device can initiate the action absent user interaction with the display, a preventative action to the medical device, or initiate an alarm on the mobile device to alert the user to a result of the analysis.

Additionally, the mobile device can monitor trends in the data generated by the medical device and update the data as the trends change. The trends can be displayed on the display of the mobile device. For example, a medical metric such as an electrocardiogram (EKG) of a first person may not be the same as an EKG of a second person. By receiving real-time data from a medical device, a trend that is specific to a user of the medical device can be established by the mobile device and therefore reported to a user.

In another example embodiment, the data can be analyzed by a different memory device and/or controller. The different memory device can be included in network relationship such as a cloud communicatively coupled to the mobile device. The cloud can store data about the medical device, data about the user such as historical data, etc. The memory device of the cloud can analyze the data about the medical device by comparing the data received about the medical device and data generated by the medical device. Based on the comparison, the memory device of the cloud can transmit a signal to the mobile device, and the mobile device can initiate a preventative action to the medical device or initiate an alarm on the mobile device to alert the user to a result of the analysis.

In the following detailed description of the present disclosure, reference is made to the accompanying drawings that form a part hereof, and in which is shown by way of illustration how one or more embodiments of the disclosure can be practiced. These embodiments are described in sufficient detail to enable those of ordinary skill in the art to practice the embodiments of this disclosure, and it is to be understood that other embodiments can be utilized and that process, electrical, and structural changes can be made without departing from the scope of the present disclosure.

As used herein, designators such as "N," "M," "P," "Q," etc., particularly with respect to reference numerals in the drawings, indicate that a number of the particular feature so designation can be included. It is also to be understood that the terminology used herein is for the purpose of describing particular embodiments only and is not intended to be limiting. As used herein, the singular forms "a," "an," and "the" can include both singular and plural referents, unless the context clearly dictates otherwise. In addition, "a number of," "at least one," and "one or more" (e.g., a number of memory devices) can refer to one or more memory devices, whereas a "plurality of" is intended to refer to more than one of such things. Furthermore, the words "can" and "may" are used throughout this application in a permissive sense (i.e., having the potential to, being able to), not in a mandatory sense (i.e., must). The term "include," and derivations thereof, means "including, but not limited to." The terms "coupled," and "coupling" mean to be directly or indirectly connected physically or for access to and movement (transmission) of commands and/or data, as appropriate to the context. The terms "data" and "data values" are used interchangeably herein and can have the same meaning, as appropriate to the context.

The figures herein follow a numbering convention in which the first digit or digits correspond to the figure number and the remaining digits identify an element or component in the figure. Similar elements or components between different figures can be identified by the use of similar digits. For example, 106 can reference element "06" in FIG. 1, and a similar element can be referenced as 206 in FIG. 2. A group or plurality of similar elements or components can generally be referred to herein with a single element number. For example, a plurality of reference elements 430-1, . . . , 430-N (e.g., 430-1 to 430-N) can be referred to generally as 430. As will be appreciated, elements shown in the various embodiments herein can be added, exchanged, and/or eliminated so as to provide a number of additional embodiments of the present disclosure. In addition, the proportion and/or the relative scale of the elements provided in the figures are intended to illustrate certain embodiments of the present disclosure and should not be taken in a limiting sense.

Figure 1:
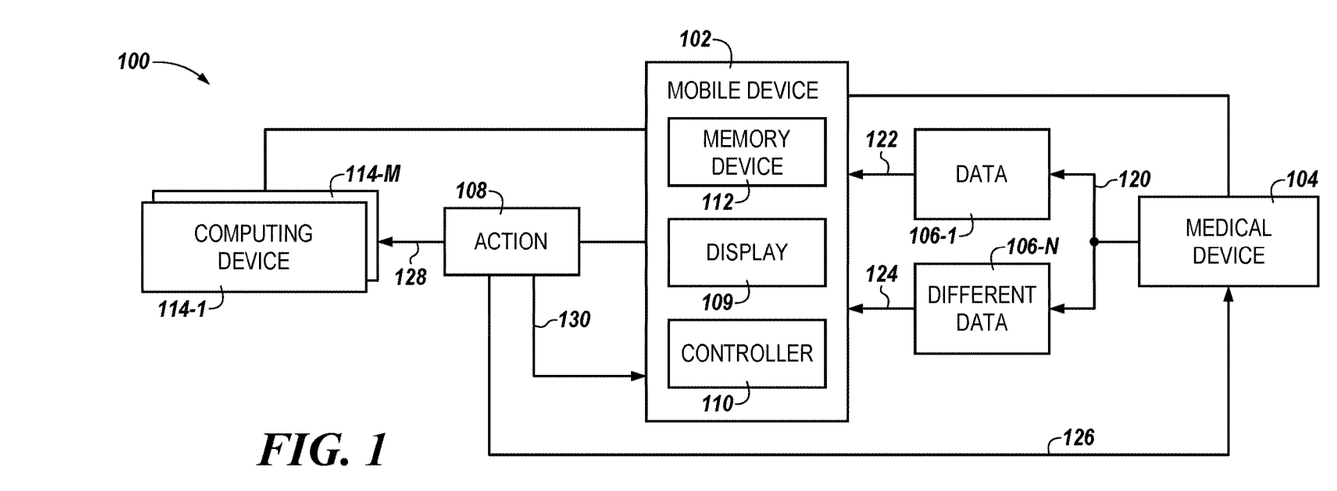
FIG. 1 is a functional block diagram in the form of a computing system including an apparatus in the form of a mobile device in accordance with a number of embodiments of the present disclosure.

FIG. 1 is a functional block diagram in the form of a computing system 100 including an apparatus in the form of a mobile device 102 in accordance with a number of embodiments of the present disclosure. As used herein, an "apparatus" can refer to, but is not limited to, any of a variety of structures or combinations of structures, such as a circuit or circuitry, a die or dice, a module or modules, a device or devices, or a system or systems, for example. The mobile device 102 can include a memory device 112 and a controller 110.

The memory device 112 can include different types of memory. There are many different types of memory including volatile and non-volatile memory. For example, non-volatile memory can provide persistent data by retaining written data when not powered, and non-volatile memory types can include NAND flash memory, NOR flash memory, read only memory (ROM), Electrically Erasable Programmable ROM (EEPROM), Erasable Programmable ROM (EPROM), and Storage Class Memory (SCM) that can include resistance variable memory, such as phase change random access memory (PCRAM), three-dimensional cross-point memory (e.g., 3D XPoint™), resistive random access memory (RRAM), ferroelectric random access memory (FeRAM), magnetoresistive random access memory (MRAM), and programmable conductive memory, among other types of memory. Volatile memory can require power to maintain its data (e.g., host data, error data, etc.), and volatile memory types can include random-access memory (RAM), dynamic random access memory (DRAM), and static random access memory (SRAM), among others.

The mobile device 102 can be a computing device. Some examples of a computing device are a wearable computing device (e.g., a smartwatch, smart glasses, etc.), a personal laptop computer, a tablet, a phablet, a desktop computer, a computing device located in a vehicle, a digital camera, a mobile telephone (e.g., a smartphone), an internet-of-things (IoT) enabled device, a memory card reader, or graphics processing unit (e.g., a video card), among various other types of computing devices. The mobile device 102 can include a system motherboard and/or backplane and can include a number of memory access devices such as a number of processing resources (e.g., one or more processors, microprocessors, image processor, and/or some other type of controlling circuitry). One of ordinary skill in the art will appreciate that "a processor" can intend one or more processors, such as a parallel processing system, a number of coprocessors, etc.

As used herein an "IoT enabled device" can refer to devices embedded with electronics, software, sensors, actuators, and/or network connectivity which enable such devices to connect to a network and/or exchange data. Examples of IoT enabled devices include mobile phones, smart phones, tablets, phablets, computing devices, implantable devices, vehicles, home appliances, smart home devices, monitoring devices, wearable devices, devices enabling intelligent shopping systems, among other cyber-physical systems.

The mobile device 102 can include a display 109. The display 109 may be a touchscreen display of the mobile device 102 such as a smartwatch. The controller 110 can be communicatively coupled to the memory device 112 and/or the display 109. The display 109 can display analyzed data to a user of the medical device 104. The display 109 can provide real-time information to the user of the medical device. As will be further described in connection with FIG. 3, the display 109 can display a number of options to transmit the analyzed data and/or to inform the user of the analyzed data. The mobile device 102 can be coupled to other computing devices 114-1 to 114-M. Some examples of the other computing devices 114 include a computing device included in a medical facility such as a hospital, a different mobile device related to the user of the medical device 104 (e.g., computing device of an emergency contact person), among others.

As illustrated in FIG. 1, the mobile device 102 can include a display 109 and be coupled to a medical device 104. In some embodiments, the medical device 104 can be an implantable medical device 104. An implantable medical device can include a medical device that is in contact with a portion of a user's body such that is partially visible, completely visible, or not visible. An implantable medical device can include a medical device that is selectively removeable. Some examples, of medical devices include, implantable cardioverter defibrillators (ICDs), pacemakers, glucose detecting contact lenses, insulin pumps, cochlear implants, hearing aids, prothesis (e.g., implantable prothesis), a diaphragm pacing system, among others.

The medical device 104 can transmit data 106-1 to 106-N as indicated by the arrow 120. The data 106-1 may be baseline dataset. As used herein, a baseline dataset can include identification data about the medical device (e.g., manufacturing information, serial number, etc.). A baseline dataset can also include information about the user of the medical device 104. For example, the baseline dataset can include information related to a user of the medical device 104, where the information is related to at least one of family history, geographic location, a health of the user, habits of the user, or any combination thereof. The data 106-1 can be displayed on the display 109.

The medical device 104 can generate and transmit different data 106-N. The different data 106-N can be displayed on the display 109. The different data 106-N can include data collected by the medical device 104 as the medical device 104 is operating. For example, the medical device 104 may be an ICD, and the different data 106-N generated may be heartrate information (e.g., an EKG). The different data 106-N can be transmitted during a predetermined intervals, or during predetermined periods of time, or combinations thereof. The medical device 104 can transmit the data 106-1 to the mobile device 102 as indicated by the arrow 122 and can transmit the different data 106-N as indicated by the arrow 124.

In an example embodiment, and as illustrated in FIG. 1, the mobile device 102 can include a controller 110 coupled to a memory device 112. The controller 110 can be configured to receive the data 106-1 from the medical device 104 where the data 106-1 is baseline dataset related to the medical device 104 and/or the user of the medical device 104. For example, the medical device 104 can be an implantable medical device 104 and the data 106-1 from the medical device 104 is at least one of an identifier of the medical device 104 (e.g., manufacturer information), an identifier of a user of the medical device 104 (e.g., name, address, emergency contact information), a medical facility associated with the medical device 104 (e.g., doctor and/or hospital information), family history of the user of the medical device 104, or combinations thereof. The controller 110 can store the data 106-1 in the memory device 112.

Continuing with the above example, the controller 110 can be configured to receive different data 106-N from the medical device 104, where the different data 106-N is received from the medical device 104 as the different data 106-N is generated by the medical device 104. The data 106-1 and the different data 106-N can be displayed on the display 109. For instance, a medical device 104 such as an ICD may monitor the heartbeat of the user in which the ICD is implanted. The ICD may generate data 106-N about the heartbeats and transmit them to the mobile device 102 periodically, consistently, during predetermined intervals, and/or during predetermined periods of time, etc. and the generated data 106N can be visible on the display 109. The controller 110 can store the different data 106-N in the memory device 112. Because the mobile device 102 has received and stored the data 106-1 (e.g., the baseline dataset) and the different data 106-N in the memory device 112, the controller 110 can analyze the data 106-1 from the medical device 104 and the different data 106-N generated by the medical device 104.

For example, the analysis can include a comparison of the data 106-1 and the different data 106-N. The controller 110 can be configured with one or more thresholds that can determine how the comparison can affect the medical device. In other examples, the controller 110 can analyze the different data 106-N by comparing it to the one or more configured thresholds. For example, the controller 110 can compare the received different data 106-N with the one or more thresholds and initiate an action based on the different data being above or below a determined threshold. In some examples, the threshold may be determined based at least in part on the data 106-1 (e.g., the baseline dataset). For instance, the baseline dataset can inform the controller 110 what sufficient homeostasis is for the user of the medical device 104. Because the medical device 104 is transmitting data 106-1 and different data 106-N the controller 110 can establish what is typical for the user of the medical device 104 and establish thresholds accordingly.

The analyzed data can be presented on the display 109 of the mobile device 102 such that a user can view the analyzed data. In some examples, the user may select from options visible on the display 109. For example, the controller 110 can perform an action based on input received from a user selecting an option from the display 109. The controller 110 can perform an action 108 based on the analyzed data 106-1 from the medical device 104 and the different data 106-N generated by the medical device 104. An action 108 can be a notification, and the notification can be transmitted to a computing device 114 (as indicated by the arrow 128) and include information about the medical device 104. The notification may be an electronic notification such as a text message, an email, an automated phone call, a social media message, etc. The notification can be transmitted to a computing device 114 such as a computing device within a medical facility, a computing device 114 belonging to an emergency contact determined by the controller 110 receiving the baseline dataset, and/or a computing device belonging to the user of the medical device 104 (e.g., a separate computing device than the mobile device 102).

In another example embodiment, the action 108 is an alarm (transmitted as indicated by the arrow 130), and the alarm is generated by the mobile device 102 in the form of an audible signal, a vibration, an electronic communication, an electric shock, or any combination thereof. For instance, in an example where the mobile device 102 is a smartwatch worn by the user of the medical device 104, the alarm can be generated by the smartwatch such that the user is made aware of the alarm. Said differently, the medical device 104 can be an ICD implanted in a user, and the action 108 can be an alarm of the smartwatch worn by the user. In this way, the user received real-time data about the medical device 104 and can view the real-time data on the display 109. In other examples, the action 108 is a signal transmitted (as indicated by the arrow 126) to the medical device 104, and the medical device 104 generates electricity (or another operation, releases medication, glucose, insulin, etc.) responsive to the receipt of the signal.

In a non-limiting example, the medical device 104 can be an ICD and the action 108 can initiate a delivery of an electric shock by the ICD. For instance, in an example where the medical device 104 is an ICD, the action 108 can include transmitting a signal from the mobile device 102 to the medical device 104 to initiate an electric shock to the user of the implanted medical device 104 (e.g., the ICD). In another non-limiting example, the medical device 104 can be an insulin pump (or glucose pump) and the action 108 can initiate a delivery of insulin and/or glucose by the insulin pump.

In another example embodiment, the action 108 can include and/or initiate updating the baseline data stored by the memory device 112. As mentioned above, the controller 110 can be configured to store the baseline dataset in the memory device 112 coupled to the mobile device and update the baseline dataset based at least in part on the different data 106-N received from the medical device 104, the action 108, or both.

Figure 2:
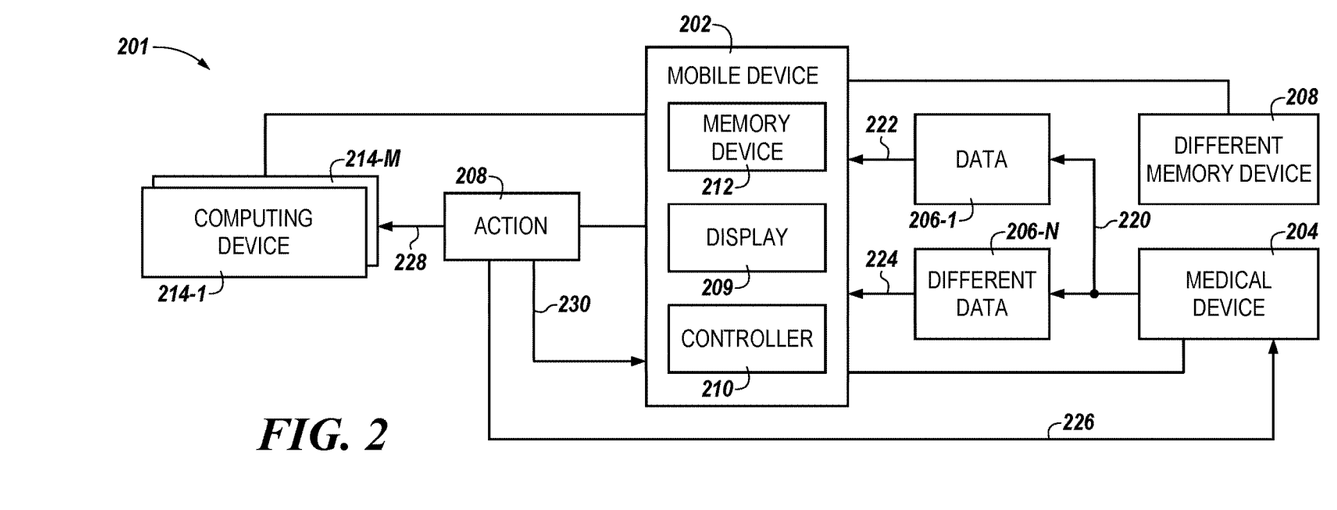
FIG. 2 is a functional block diagram in the form of a computing system including a mobile device and a plurality of memory devices in accordance with a number of embodiments of the present disclosure.

FIG. 2 is a functional block diagram in the form of a computing system 201 including a mobile device 202 and a plurality of memory devices in accordance with a number of embodiments of the present disclosure. The mobile device 202 includes a controller 210, a memory device 212, and a display 209 which can be analogous to the mobile device 102, the controller 110, the display 109, and the memory device 112 described in connection with FIG. 1. The mobile device 202 can be coupled to a medical device 204 which can be analogous to the medical device 104 of FIG. 1. The medical device 204 can transmit data 206-1 and different data 206-N as indicated by the arrow 220 and can be analogous to the data 106-1 and the different data 106-N. The mobile device 202 can be coupled to one or more other computing devices 214-1 and/or 214-M which can be analogous to the other computing devices 114 described in connection with FIG. 1. The mobile device 202 can be further coupled to a different memory device 208. The different memory device 208 may be in a wired or wireless network relationship with the mobile device 202 and/or the other computing devices 214.

As used herein, the term "network relationship" can, for example, refer to a local area network (LAN), VLAN, wide area network (WAN), personal area network (PAN), a distributed computing environment (e.g., a cloud computing environment), storage area network (SAN), Metropolitan area network (MAN), a cellular communications network, and/or the Internet, among other types of network relationships. In some embodiments, the different memory device 208 can be included on a network device such as a server computing device (e.g., on-premise server, private, public, or hybrid cloud server) that comprises a hardware or a combination of hardware and software that can process and/or display network-related information. In some implementations, a network device may refer to an access point acting as a virtual master network controller among a cluster of access points. The different memory device 208 can include circuitry and/or logic to store the data 206-1, the different data 206-N, and/or to perform analysis on the respective data.

For example, the mobile device 202 may be a smartwatch worn by a user of the medical device 204, where the medical device 204 is implanted in the user. The smartwatch can include a display 209 to provide real-time data about the implanted medical device 204 to the user. The user can utilize the smartwatch to transmit data 206-1 (e.g., baseline data) via the display 209, the different data 206-N (e.g., data as it is generated by the medical device), to the different memory device 208. In some incidences, the mobile device 202 may be relatively small (e.g., a smartwatch) and the memory device 212 may not have the capacity to store all of the data generated by the medical device 204. As such, the mobile device 202 may be in a network relationship with a different memory device 208 which can increase storage capacity.

For example, the computing system 201 can include a memory device 212 coupled to a controller 210 included in a mobile device 202. The medical device 204 can be coupled to the mobile device 202, where the medical device 204 is to provide information about the medical device 204 to the mobile device 202 where the medical device 204 is implantable. The mobile device can include a display 209 to provide the user of the medical device 204 with the data 206-1, the different data 206-N, and/or analyzed data. A different memory device 208 can be coupled to the mobile device 202 to receive the information about the medical device 204 from the mobile device 202.

The controller 210 can be configured to receive data 206-1 from the medical device 204 (as indicated by the arrow 222), where the controller 210 can store the data 206-1 (e.g., baseline dataset) in the memory device 212 coupled to the controller 210 as a baseline dataset related to the medical device 204. The controller 210 can transmit the data 206-1 from the medical device 204 to the different memory device 208. In some examples, the user can transmit the data 206-1 from the mobile device 202 to the different memory device 208 by selecting an option on the display 209. The different memory device 208 can store the baseline dataset.

The controller 210 can receive different data 206-N (as indicated by the arrow 224) from the medical device 204, where the different data 206-N can be received from the medical device 204 as the different data 206-N is generated by the medical device 204. Said differently, as the medical device 204 generate data (e.g., heartbeat, blood sugar levels, etc.) about the user and/or the medical device 204, the medical device 204 can transmit the different data 206-N as it is generated. In this way, the user of the mobile device 202 can receive real-time data about the medical device 204. In some examples, the user can transmit the different data 206-N from the mobile device 202 to the different memory device 208 by selecting an option on the display 209. The controller 210 can transmit the different data 206-N from the medical device 204 to the different memory device 208.

As mentioned, the different memory device 208 may include a capacity to store a larger amount of data when compared to the memory device 212 of the mobile device 202 (e.g., a smartwatch). The different memory device 208 may store historical information related to a user of the medical device, where the information is can be related to at least one of family history, geographic location, a health of the user, habits of the user, or any combination thereof. In some examples, the user can input the historical data into the mobile device 202 using the display 209 and transmit the historical data to the different memory device 208 using the display 209.

The different memory device 208 can perform an analysis of the data 206-1 and the different data 206-N. The analysis can include a comparison of the data 206-1, to the different data 206-N, and/or any historical information as mentioned above. The different memory device 208 can transmit the analyzed data to the mobile device 202. The transmitted analyzed data can be visible to the user on the display 209 as the user receives the analyzed data. For example, the different memory device 208 can push a notification (e.g., a text message, an email, etc.) related to the medical device 204 to the mobile device 202 (e.g., a smartwatch) responsive to the analyzed data. The notification can be viewed by a user on the display 209. In this way, the user of the medical device 204 wearing the smartwatch can receive real time data about the medical device 204.

The controller 210 can receive the analyzed data from the different memory device 208 responsive to it performing an analysis on the data 206-1 from the medical device 204 and the different data 206-N generated by the medical device 204. The controller 210 can initiate an action 208 based on the analyzed data received from the different memory device 208. In some examples, the action can be selected from the display 209 by the user. An action 208 can be a notification, and the notification can be transmitted to a computing device 214 (as indicated by the arrow 228) and include information about the medical device 204. The notification may be an electronic notification such as a text message, an email, an automated phone call, a social media message, etc. The notification can be transmitted to a computing device 214 such as a computing device within a medical facility, a computing device belonging to an emergency contact determined by the controller 210 receiving the baseline dataset, and/or a computing device 214 belonging to the user of the medical device 204 (e.g., a separate computing device than the mobile device 202). In another example embodiment, the action 208 is an alarm (transmitted as indicated by the arrow 230), and the alarm is generated by the mobile device 202 in the form of an audible signal, a vibration, an electronic communication, an electric shock, or any combination thereof. In other examples, the action 208 is a signal transmitted (as indicated by the arrow 226) to the medical device 204. In some examples, the signal transmitted to the medical device 204 initiates the medical device 204 to administer medication (e.g., insulin from an insulin pump, etc.).

In some examples, embodiments, the action 208 can include the controller 210 initiating an update to the baseline dataset based on the analyzed data, the action 208, or both. For example, the mobile device 202 may generate an action 208 in the form of an alarm. A user may indicate that the alarm is not necessary, and the baseline data can be updated to reflect that the analyzed data resulted in an unnecessary alarm. In some examples, the update to the baseline dataset can include changing the thresholds. These methods can provide a user of the medical device 204 with real-time data from the medical device 204 as the user operates in their daily life.

Figure 3:
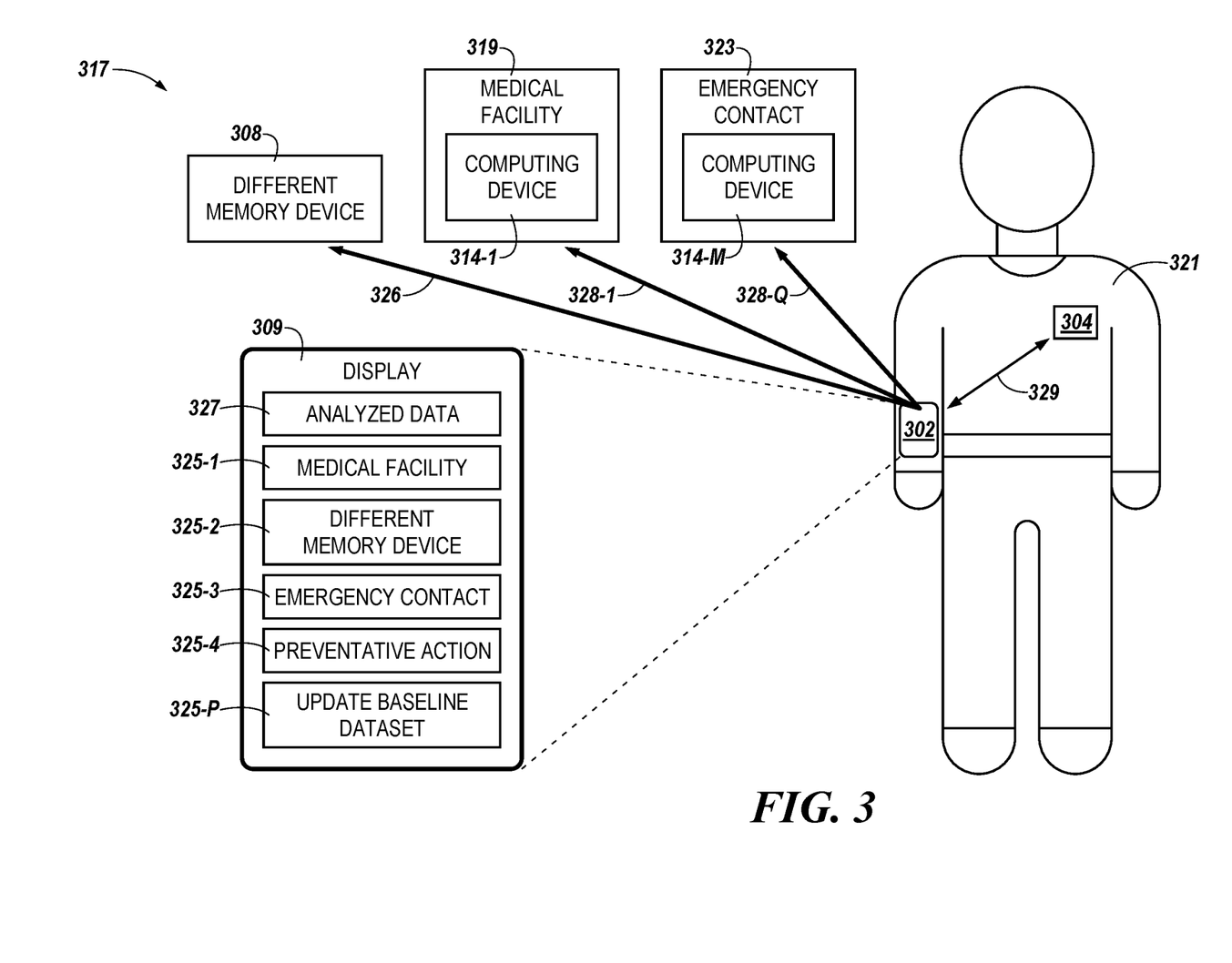
FIG. 3 is a diagram representing an example display of a mobile device for medical device data analysis in accordance with a number of embodiments of the present disclosure.

FIG. 3 is a diagram 317 representing an example display 309 of a mobile device 302 for medical device data analysis in accordance with a number of embodiments of the present disclosure. FIG. 3 includes a user 321 utilizing a wearable mobile device 302 in the form of a smartwatch. The mobile device 302 is communicatively coupled to a medical device 304 as indicated by the arrow 329. The mobile device 302 and the medical device 304 can be analogous to the mobile device 102 and the medical device 104 of FIG. 1. The medical device 304 may be an implantable medical device implanted into the user 321. The mobile device 302 may be communicatively coupled to a computing device 314-1 included in a medical facility 319 and a computing device 314-M related to an emergency contact person. The mobile device 302 can be communicatively coupled to a different memory device 308 which can be analogous to the different memory device 208 of FIG. 2.

FIG. 3 illustrates a display 309 of the mobile device 302. For clarity and understanding of the detailed description, the display 309 is enlarged. The display 309 can include options for the user to select based on data related to the medical device 304. For example, data (e.g., the data 106-1 and/or the different data 106-N) can be generated by the medical device 304 and transmitted to the mobile device 302 as indicated by the arrow 329. The mobile device 302 can analyze the data using a controller analogous to the controller 110 of FIG. 1. The analyzed data 327 can be visible on the display 309. The user 321 can view the analyzed data 327 and initiate an action using the display 309.

For example, the user 321 can initiate an action by selecting the option for the medical facility 325-1 and the mobile device can transmit the analyzed data 327 to the computing device 314-1 included in the medical facility 319 as indicated by the arrow 328-1. In some examples, the mobile device 302 transmits the data generated by the medical device 304 to the different memory device 308 for analysis as indicated by the arrow 326, and the mobile device 302 can display the data analyzed by the different memory device 308 to on the display 309.

In another non-limiting embodiment, the user 321 can initiate an action by selecting the option for the different memory device 325-2 and the mobile device can transmit the analyzed data 327 to the different memory device 325-2 to be stored. In some examples, a medical facility related to the user may have access to the different memory device 308. In some examples, the mobile device 302 transmits the data generated by the medical device 304 to the different memory device 308 for analysis as indicated by the arrow 326, and the mobile device 302 can display the data analyzed by the different memory device 308 to on the display 309.

In another non-limiting embodiment, the user 321 can initiate an action by selecting the option for the emergency contact 325-3 and the mobile device 302 can transmit the analyzed data 327 to the computing device 314-M corresponding to the emergency contact 323 as indicated by the arrow 328-Q. In some examples, the emergency contact may be a person known to the user 321. In some examples, the computing device 314-M may be a different mobile device belonging to the emergency contact. In some examples, the mobile device 302 transmits the data generated by the medical device 304 to the different memory device 308 for analysis as indicated by the arrow 326, and the mobile device 302 can display the data analyzed by the different memory device 308 to on the display 309.

In another non-limiting embodiment, the user 321 can initiate an action by selecting the option for the preventative action 325-4 and the mobile device 302 can transmit a signal to the medical device 304 as indicated by the arrow 329 to initiate the preventative action. In some examples, the preventive action is a signal to the medical device to administer an electronic shock, glucose, and/or insulin, or other medications. In some examples, the preventative action may be an alarm or an alert to the user. For example, if the medical device 304 is a device to monitor heartrate, the preventive action may be an alert to suggest to the user 321 to rest when the heartrate is above or below a threshold.

In another non-limiting embodiment, the user 321 can initiate an action by selecting the option to update a baseline dataset and the mobile device 302 can update a baseline dataset or alter a threshold based on the user interacting with the display 309 to update the baseline dataset. For example, if the user 321 moves to a different climate with different environmental conditions, the user 321 can update the baseline dataset based on the analyzed data 327.

Figure 4:
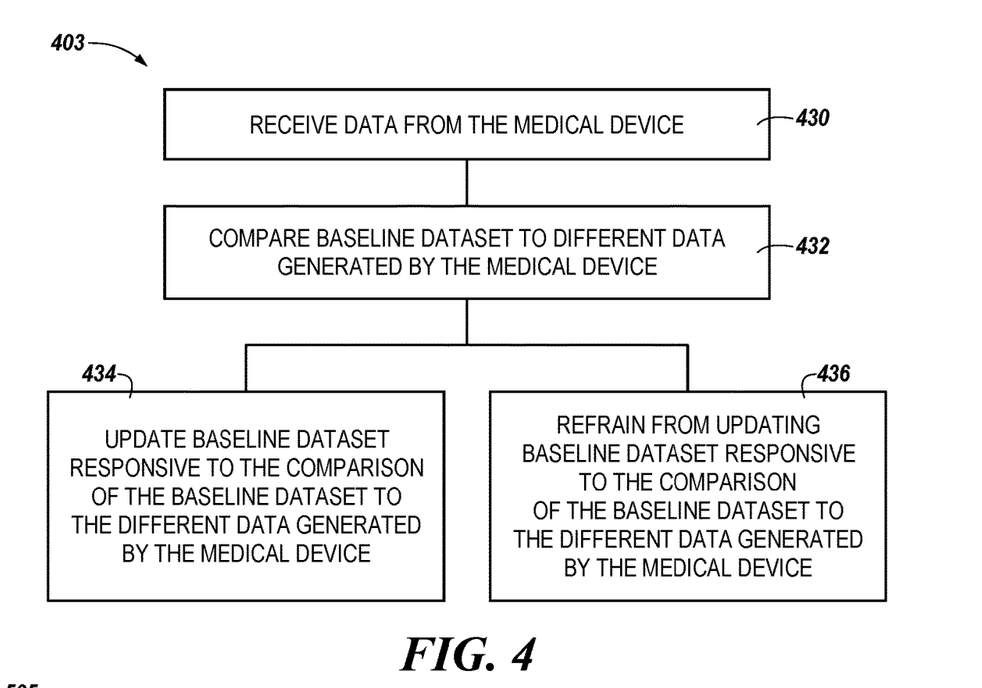
FIG. 4 is a flow diagram representing an example of medical device data analysis in accordance with a number of embodiments of the present disclosure.

FIG. 4 is a flow diagram 403 representing an example of medical device data analysis in accordance with a number of embodiments of the present disclosure. The flow diagram 403 describes a medical device (e.g., the medical device 104 described in connection with FIG. 1). The medical device can be an implantable medical device and can transmit data (e.g., the data 106-1 and/or the different data 106-N of FIG. 1) to a mobile device (e.g., the mobile device 102 of FIG. 1). In some examples, the mobile device can be a smartwatch and can include a display (e.g., the display 309 of FIG. 3). In some examples, the mobile device can transmit the data and/or different data to a different memory device (e.g., the different memory device 208 of FIG. 2) for analysis. In some examples, the different memory device is wirelessly coupled to the mobile device and performs the analysis on the respective data by comparing the baseline dataset to the different data generated by the medical device. The analysis may cause a controller (e.g., the controller 110 of FIG. 1) to update the baseline dataset.

For example, at 430, the controller and/or the different memory device networked with the controller can receive data from the medical device. The data received can be a baseline dataset and/or different data that was transmitted as it was generated by the medical device. At block 432 the controller and/or the different memory device can analyze the respective data and compare the baseline dataset to different data generated by the medical device. The comparison can determine trends in the data of the medical device.

For example, if the medical device is an ICD implanted in a user, initial baseline datasets may include a particular heartrate, and as time passes, the ICD can generate heartbeat data that can be compared to the baseline particular heartbeat data and actions (e.g., an action 108 of FIG. 1) can be initiated based on the comparison. However, the user may change their lifestyle that results in different baseline datasets. For example, if the user begins exercising on a regular basis, the baseline dataset may change because the heartrate of the user may change. In this example, at block 434 the controller and/or the different memory device can update the baseline dataset responsive to the comparison of the baseline dataset to the different data generated by the medical device. In this way, the comparison of the baseline dataset and the data generated by the ICD may be updated.

In other examples, the baseline dataset may not be updated because the comparison resulted in an analysis that was not consistent with a trend. For instance, if the user has a problematic heart episode, the controller may initiate an action (e.g., an electric shock). In this incidence, the baseline dataset would not be updated as it is not indicative of a regular trend. In other words, at block 436, the controller and/or the different memory device can refrain from updating the baseline dataset responsive to the comparison of the baseline dataset to the different data generated by the medical device.

Figure 5:
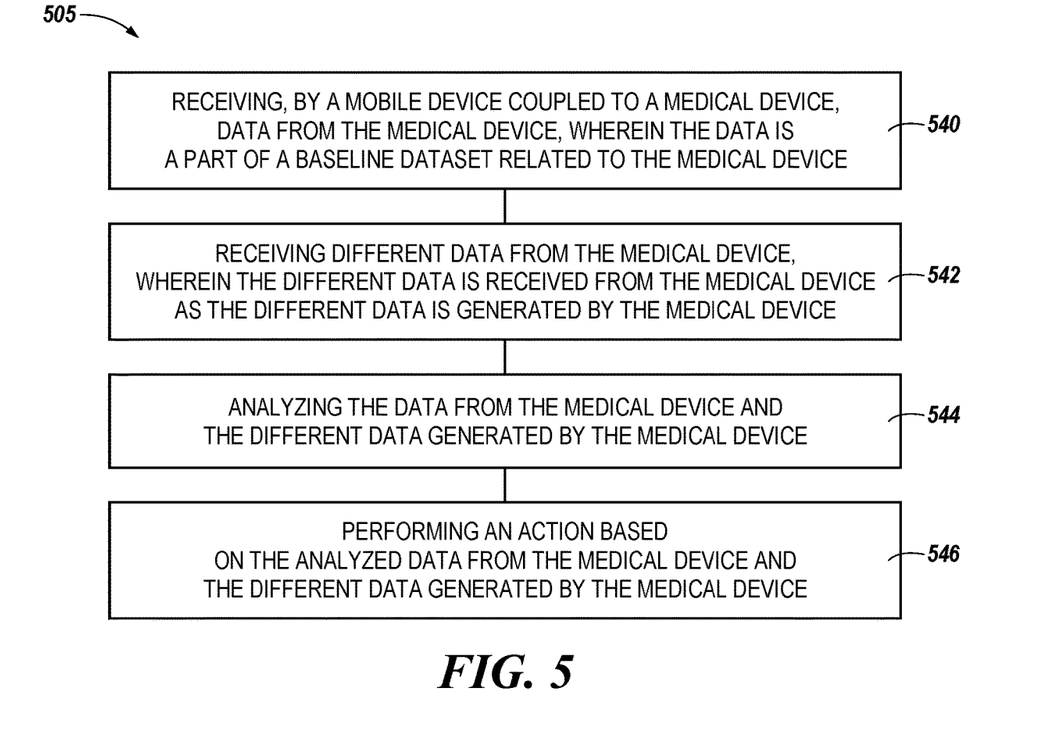
FIG. 5 is a flow diagram representing an example method for medical device data analysis in accordance with a number of embodiments of the present disclosure.

FIG. 5 is a flow diagram representing an example method 505 for medical device data analysis in accordance with a number of embodiments of the present disclosure. At block 540, the method 505 can include receiving, by a mobile device (e.g., the mobile device 102 of FIG. 1) coupled to a medical device (e.g., the medical device 104 of FIG. 1), data (e.g., the data 106-1 of FIG. 1) from the medical device, wherein the data is a part of a baseline dataset related to the medical device. The medical device can be implanted in a person and can be wirelessly coupled to the mobile device. The baseline dataset can include identification data about the medical device (e.g., manufacturing information, serial number, etc.). A baseline dataset can also include information about the user of the medical device. Different data (e.g., the different data 106-N of FIG. 1) can be received by the mobile device. Data generated by the medical device can be viewed by a user on a display (e.g., the display 309 of FIG. 3).

For example, at block 542, the method 505 includes receiving different data from the medical device, wherein the different data is received from the medical device as the different data is generated by the medical device. The different data can be data transmitted to the mobile device in real-time. In this way, a user of the medical device can view respective data about the medical device. The controller (e.g., the controller 110 of FIG. 1) of the mobile device may analyze the different data as it is received by the mobile device.

For example, at block 544, the method 505 includes analyzing the data from the medical device and the different data generated by the medical device. The baseline dataset may determine a threshold related to the medical device. The analysis of the different data can include the controller comparing the different data received form the medical device to a threshold established by the baseline dataset. The controller may initiate an action based on the analysis.

For example, at block 546, the method 505 includes performing an action based on the analyzed data from the medical device and the different data generated by the medical device. The action can be performed at the mobile device or medical device, or both. In an example embodiment, the action can include transmitting the analyzed data to a computing device (e.g., the computing device 114-1 of FIG. 1), where the computing device is within a medical center. The analyzed data can be transmitted to a computing device that is associated with a medical center related to the user of the medical device. In this example, the real-time data generated by the medical device can be reported to a medical center. In another example embodiment, the action can include transmitting the analyzed data to another mobile device (e.g., the computing device 114-M of FIG. 1) corresponding to a user of the medical device.

In this example, the computing device may be a mobile device related to an emergency contact of the user and the real-time data generated by the medical device can be transmitted to another person in the event that the user of the medical device is incapacitated. In yet another example embodiment, the action can include assessing a health of a user of the medical device responsive to the analyzed data and initiating an operation of the medical device based on the assessment. In this example, the controller can initiate an operation of the medical device (e.g., the dispensing of insulin, or an electric shock.

Figure 6:
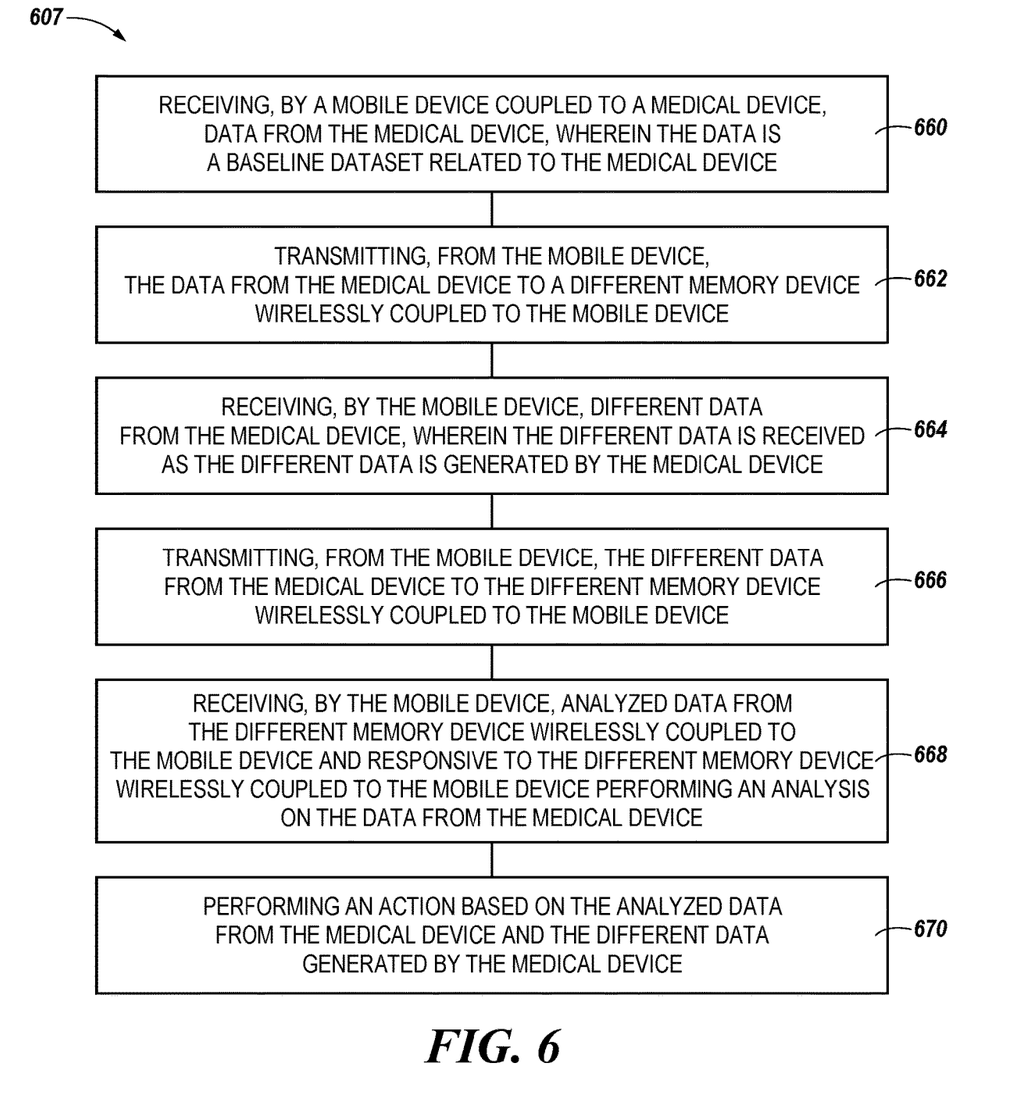
FIG. 6 is a flow diagram representing an example method for medical device data analysis in accordance with a number of embodiments of the present disclosure.

FIG. 6 is a flow diagram representing an example method 607 for medical device data analysis in accordance with a number of embodiments of the present disclosure. At block 660, the method 607 includes receiving, by a mobile device (e.g., the mobile device 102 of FIG. 1) coupled to a medical device (e.g., the medical device 104 of FIG. 1), data from the medical device, wherein the data is a baseline dataset related to the medical device. The medical device can be implanted in a person and can be wirelessly coupled to the mobile device. Data generated by the medical device can be viewed by a user on a display (e.g., the display 309 of FIG. 3).

At block 662, the method 607 includes transmitting, from the mobile device, the data from the medical device to a different memory device (e.g., the different memory device 208 of FIG. 2) wirelessly coupled to the mobile device. In some examples, the different memory device wirelessly coupled to the mobile device is located on a private cloud and communicatively coupled to at least one of the medical device, a computing device of a medical facility (e.g., the computing device 114 of FIG. 1), or both.

At block 664, the method 607 includes, receiving, by the mobile device, different data (e.g., the different data 106-N) from the medical device, wherein the different data is received as the different data is generated by the medical device. In this way, real-time data can be received by the mobile device (e.g., a smartwatch worn by the user of the medical device).

At block 666, the method 607 includes, transmitting, from the mobile device, the different data from the medical device to the different memory device wirelessly coupled to the mobile device. The mobile device can transmit the different data to the different memory device for analysis.

At block 668, the method 607 includes receiving, by the mobile device, analyzed data from the different memory device wirelessly coupled to the mobile device and responsive to the different memory device wirelessly coupled to the mobile device performing an analysis on the data from the medical device. The different memory device can perform the analysis and provide the analyzed data to the mobile device to initiate an action (e.g., the action 108 of FIG. 1).

At block 670, the method 607 includes performing an action based on the analyzed data from the medical device and the different data generated by the medical device. The action can be performed at the mobile device or medical device, or both. In some examples, based on the analysis, the mobile device can initiate a preventative action to the medical device, or initiate an alarm on the mobile device to alert the user to a result of the analysis.

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and processes are used. Therefore, the scope of one or more embodiments of the present disclosure should be determined with reference to the appended claims, along with the full range of equivalents to which such claims are entitled.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method, comprising:
    receiving, by a mobile device comprising a smartwatch including a display and wirelessly coupled to a medical device implanted in a user, data from the implanted medical device, wherein the data is a part of a baseline dataset including threshold homeostasis levels from the user that establish the user's baseline dataset and further including identification data about the medical device, user family history, medical device geographic location, a health of the user, and habits of the user, and wherein the baseline dataset is related to an operation of the implanted medical device performed on the user, wherein the implanted medical device is an implantable cardioverter-defibrillator (ICD), configuring the mobile device with the threshold homeostasis levels;

receiving different data from the implanted medical device, wherein the different data is received from the implanted medical device as the different data is generated by the implanted medical device;

analyzing, via comparison to the configured thresholds, the data from the implanted medical device and the different data generated by the implanted medical device in real time;

receiving, by the mobile device and responsive to the analysis, the analyzed data from the implanted medical device;

establishing a trend specific to the user of the implanted medical device based on the analyzed data from the implanted medical device and the different data generated by the implanted medical device;

displaying, via the display of the smartwatch, the established trend;

initiating, via the display of the smartwatch, a delivery of an action comprising an electric shock by the implanted medical device;

the implanted medical device receiving the action and administering the electric shock to the user based on the established trend, the analyzed data from the implanted medical device, the configured thresholds, and the different data generated by the implanted medical device; and monitoring additional trends in the different data generated by the implanted medical device, comparing the configured thresholds of the baseline dataset to the different data and updating the different data in response to the baseline dataset falling within one trend of a group of additional trends;

utilizing the different data to determine that an emergency contact for the user should be notified; and sending, via the mobile device, a notification to the emergency contact.

2. The method of claim 1, further comprising:

receiving, at a memory device coupled to the mobile device, the baseline dataset;

storing the baseline dataset including the part of the baseline dataset in the memory device coupled to the mobile device; and updating the baseline dataset based at least in part on the different data received from the implanted medical device, the action, or both.

3. The method of claim 1, further comprising transmitting the analyzed data to a computing device, wherein the computing device is within a medical center.

4. The method of claim 1, further comprising transmitting the analyzed data to another mobile device corresponding to the user of the implanted medical device.

5. The method of claim 1, further comprising:

assessing a health of the user of the medical device responsive to the analyzed data; and initiating the action of the implanted medical device based on the assessment.

6. A method, comprising:

receiving, by a mobile device comprising a smartwatch including a display and wirelessly coupled to a medical device implanted in a person, data from the implanted medical device, wherein the data is a baseline dataset including threshold homeostasis levels from the user that establish the baseline dataset and further including identification data about the medical device, user family history, medical device geographic location, a health of the user, and habits of the user, and wherein the implanted medical device is an implantable cardioverter-defibrillator (ICD);

configuring the mobile device with the threshold homeostasis levels;

transmitting, from the mobile device, the data from the implanted medical device to a different memory device wirelessly coupled to the mobile device;

receiving, by the mobile device, different data from the implanted medical device, wherein the different data is received as the different data is generated by the implanted medical device;

transmitting, from the mobile device, the different data from the implanted medical device to the different memory device wirelessly coupled to the mobile device;

analyzing, via comparison to the configured thresholds and by the different memory device wirelessly coupled to the mobile device, the data from the implanted medical device;

receiving, by the mobile device and responsive to the analysis, the analyzed data from the different memory device wirelessly coupled to the mobile device;

establishing a trend specific to the person implanted with the implanted medical device based on the analyzed data from the implanted medical device and the different data generated by the implanted medical device;

displaying, via the display of the smartwatch, the established trend;

initiating, via the display of the smartwatch, a delivery of an action by the implanted medical device comprising an electric shock by the ICD;

the implanted medical device receiving the action and administering the electric shock to the user, based on the established trend, the analyzed data from the implanted medical device, the configured thresholds, and the different data generated by the implanted medical device; and monitoring additional trends in the different data generated by the implanted medical device and updating the different data in response to the baseline dataset falling within one trend of a group of additional trends.

7. The method of claim 6, wherein the different memory device wirelessly coupled to the mobile device is located on a private cloud and communicatively coupled to at least one of the implanted medical device, a computing device of a medical facility, or both.

8. The method of claim 6, wherein the different memory device wirelessly coupled to the mobile device performs the analysis on the data by comparing the baseline dataset to the different data generated by the implanted medical device.

9. The method of claim 8, further comprising updating the baseline dataset responsive to the comparison of the baseline dataset to the different data generated by the implanted medical device.

10. The method of claim 8, further comprising refraining from updating the baseline dataset responsive to the comparison of the baseline dataset to the different data generated by the implanted medical device.

11. A system comprising:
a mobile device comprising a smartwatch including a display and coupled to a memory device,
the memory device comprising instructions executable to cause the mobile device to:
receive data from a medical device comprising an implantable cardioverter-defibrillator (ICD) coupled to the memory device, wherein the data is a baseline related to the medical device and includes threshold homeostasis levels from the user that establish the baseline user health dataset and further includes identification data about the medical device, user family history, medical device geographic location, a health of the user, and habits of the user;
configure with the threshold homeostasis levels;
receive different data from the medical device, wherein the different data is received from the medical device as the different data is generated by the medical device;
analyze the data from the medical device and the different data generated by the medical device via comparison to the configured thresholds;
establish a trend specific to a user of the medical device based on the analyzed data from the medical device and the different data generated by the medical device;
displaying, via the display of the smartwatch, the established trend; and
initiate delivery of an action, via the smartwatch display, to the medical device comprising an electric shock by the ICD based on the established trend, the analyzed data from the medical device, the configured thresholds, and the different data generated by the medical device;
the medical device configured to:
receive the action; and
administer the electric shock to the user based on the established trend, the analyzed data from the medical device, and the different data generated by the medical device; and
the memory device configured to cause the mobile device to:
monitor additional trends in the different data generated by the implanted medical device, compare the configured thresholds of the baseline dataset to the different data and update the different data in response to the baseline dataset falling within one trend of a group of additional trends;
utilize the different data to determine that an emergency contact for the user should be notified; and
send a notification to the emergency contact.

12. The system of claim 11, wherein the data from the medical device is at least one of an identifier of the medical device, an identifier of a user of the medical device, a medical facility associated with the medical device, family history of the user of the medical device, or any combination thereof.

13. The system of claim 11, wherein:
the action further comprises a signal transmitted to the medical device; and
the medical device generates electricity responsive to the receipt of the signal.

14. The system of claim 11, wherein:
the action further comprises an alarm; and
the alarm is generated by the apparatus in the form of an audible signal, a vibration, an electronic communication or any combination thereof.

15. The system of claim 11, wherein:
the action further includes a notification; and
the notification is transmitted to a computing device and includes information about the medical device.

16. A system, comprising:
a memory device coupled to a mobile device comprising a smartwatch including a display;
a medical device coupled to the mobile device, wherein the medical device comprises an implantable cardioverter-defibrillator (ICD) and provides information about the medical device to the mobile device, and wherein the medical device is implantable;
a different memory device coupled to the mobile device configured to:
receive the information about the medical device from the mobile device;
perform an analysis on data received from the medical device using comparisons to configured threshold homeostasis levels; and
perform an analysis on different data generated by the medical device using comparisons to the configured thresholds;
the mobile device configured to:
receive the data from the medical device, wherein the data is stored in the memory device as a baseline dataset including threshold homeostasis levels from the user that establish the baseline user health dataset and further including identification data about the medical device, user family history, medical device geographic location, a health of the user, and habits of the user;
configure with the threshold homeostasis levels;
transmit the data from the medical device to the different memory device;
receive the different data from the medical device, wherein the different data is received from the medical device as the different data is generated by the medical device;
transmit the different data from the medical device to the different memory device;
responsive to the different memory device performing the analysis on the data from the medical device and the analysis on the different data generated by the medical device, receive the analyzed data from the different memory device;
initiate, via the smartwatch display, delivery of an action comprising an electric shock by the ICD based on the analyzed data from the different memory device;
establish a trend specific to a user of the medical device based on the analyzed data from the medical device and the different data generated by the medical device;
display, via the display of the smartwatch, the established trend;
update the baseline dataset based on the analyzed data, the established trend, the action, or a combination thereof in response to the baseline dataset falling within one trend of a group of additional trends;
monitor additional trends in the different data generated by the implanted medical device, compare the configured thresholds of the baseline dataset to the different data, and update the different data in response;
execute instructions to instruct the medical device to administer the electric shock to the user based on the established trend, the analyzed data from the medical device, the configured thresholds, and the different data generated by the medical device;
utilize the different data to determine that an emergency contact for the user should be notified; and send a notification to the emergency contact;
the medical device configured to:
receive the action; and
administer the electric shock to the user based on the established trend, the analyzed data from the medical device, and the different data generated by the medical device.

17. The system of claim 16, wherein:
the mobile device is a smartwatch including a display; and
the action is initiated via the display.

18. The system of claim 17, wherein the medical device is implanted in a user and the action further comprises an alarm of the smartwatch worn by the user.

19. The system of claim 17, wherein the different memory device pushes a notification related to the medical device to the smartwatch responsive to the analyzed data.

* * * * *